United States Patent [19]
Brent et al.

[11] Patent Number: 5,580,721
[45] Date of Patent: Dec. 3, 1996

[54] ASSAYS FOR INHIBITORS OF MYC ONCOPROTEIN

[75] Inventors: Roger Brent, Cambridge; Erica Golemis, Somerville; Karen F. Lech, Boston; Catherine Anderson, Cambridge, all of Mass.

[73] Assignee: The General Hospital Corporation, Boston, Mass.

[21] Appl. No.: 50,198

[22] PCT Filed: Sep. 20, 1991

[86] PCT No.: PCT/US91/06839

§ 371 Date: Oct. 7, 1993

§ 102(e) Date: Oct. 7, 1993

Related U.S. Application Data

[63] Continuation-in-part of Ser. No. 586,781, Sep. 24, 1990, abandoned.

[51] Int. Cl.[6] ............... C12Q 1/68; C12N 15/62; C12N 15/85; A61K 38/16
[52] U.S. Cl. ............... 435/6; 435/320.1; 530/358; 536/23.4
[58] Field of Search ............... 435/6, 69.7, 172.3, 435/240.1, 254.2, 320.1; 536/24.1, 23.4; 530/358

[56] References Cited

U.S. PATENT DOCUMENTS

| | | | |
|---|---|---|---|
| 4,833,080 | 5/1989 | Brent | 435/172.3 |
| 4,980,281 | 12/1990 | Housey | 435/29 |

FOREIGN PATENT DOCUMENTS

| | | |
|---|---|---|
| 325849A3 | 8/1989 | European Pat. Off. . |
| 341904A2 | 11/1989 | European Pat. Off. . |
| WO91/16456 | 10/1991 | WIPO . |

OTHER PUBLICATIONS

Ammerer; "Expression of Genes in Yeast Using the ADCI Promoter;" Methods in Enzymology, 101:192–211, 1983.
Astell et al.; "The Sequence of the DNAs Coding for the Mating–Type Loci of Saccharomyces Cerevisiae;" Cell 27:15–23, 1981.
West et al.; "Saccharomyces cerevisiae GAL1–GAL10 Divergent Promoter Region: Location and Function of the Upstream Activating Sequence $UAS_G$;" Molecular and Cellular Biology, 4:2467–2478, 1984.
Godowski et al., "Signal Transduction and Transcriptional Regulation by Glucocorticoid Receptor–LexA Fusion Proteins;" Science 241:812–816, 1988.
Busch et al. (1990), Clin. Res. 38(2), 411A, Abstract Only.
Penn et al (1990) Mol. Cell Biol. 10(9), 4961–4966.
Levine et al., Cell, 59:405–408, 1989.
Struhl, Annu. Rev. Biochem, 58:1051–1077, 1989.
Hansen et al., Cell, 53:172–173, 1988.
Struhl, Nature, 332:649–650, Apr. 14, 1988.
Lech et al., Cell, 52:179–184, 1988.
Bishop, Science, 235:305–311, 1987.
Brent et al., Cell, 43:729–736, 1985.
Giniger et al., Cell, 40:767–774, 1985.
Brent et al., Nature, 312:612–615, 1984.
Reddy et al., Proc. Natl. Acad. Sci. USA, 80:2500–2504, 1983.
Van Beveren et al., Cell, 32:1241–1255, 1983.

Primary Examiner—Mindy Fleisher
Assistant Examiner—Philip W. Carter
Attorney, Agent, or Firm—Fish & Richardson P.C.

[57] ABSTRACT

A method for the identification of compounds as inhibitors of oncoprotein action is described. A compound is identified as an inhibitor of oncoprotein action based on its ability to modulate the transcription of a reporter gene. Transcription of the reporter gene is dependent upon the binding of a fusion oncoprotein to a specific DNA binding element positioned upstream of the reporter gene promoter. The fusion oncoprotein contains a transcriptional regulatory domain from an oncoprotein and a DNA binding domain from a different protein.

21 Claims, No Drawings

ASSAYS FOR INHIBITORS OF MYC ONCOPROTEIN

This application is the national stage application of PCT application PCT/US91/06839 which is a continuation-in-part of commonly owned U.S. Ser. No. 07/586,781, filed Sep. 24, 1990, now abandoned.

BACKGROUND OF THE INVENTION

This invention relates to methods for identifying anti-cancer therapeutics.

The induction of many types of cancer is thought to be ultimately caused by the products of activated cellular oncogenes (Bishop, J. M., *Science* 235:305–310, 1987; Barbacid, M., *Ann. Rev. Biochem.* 56:779–827, 1987; Cole, M. D., *Ann. Rev. Genet.* 20:361–384, 1986; and Weinberg, R. A., *Science* 230:770–776, 1985). Such oncogenes express oncoproteins that reside in the cell, often localized to specific cellular compartments such as the nucleus, cytoplasm or cell membrane.

In particular examples, the vital and cellular fos and myc oncogenes encode the Fos and Myc proteins, respectively. Expression of a large amount of either Fos or Myc in a variety of cell types allows the cells to grow indefinitely in cell culture (reviewed in Bishop, J. M. *Cell* 42:23–38, 1985; and Weinberg, R. A., *Science* 230:770–776, 1985). Overexpression of either Fos or Myc in normal rat fibroblasts, together with expression of an activated ras oncogene product, transforms the fibroblasts and endows them with the ability to form tumors in living animals (Land, H. et al., *Nature* 304:596–601, 1983; Ruley, H. E., *Nature* 304:602–606, 1983).

Fos and Myc are examples of oncoproteins that are phosphorylated, localized to the cell nucleus, and possess an ability to alter transcription (Donner, P. et al., *Nature* 296:262–266, 1982; Watt, R. A. et al., *Mol. Cell Biol.* 5:448–456, 1985; Renz M. et al., *Nucl. Acids Res.* 5:277–292, 1987). Recent studies suggest that oncoproteins such as Fos and Myc alter gene expression and immortalize cells by regulating the promoter activity of specific target genes and thus activating or repressing transcription of those target genes (see, for example, Varmus, H. E. *Science* 238:1337–1339, 1987; Kingston, R. E. et al., *Cell* 41:3–5, 1985; Bishop, J. M., *Cell* 42:23–38, 1985; Weinberg, R. A., *Science* 230:770–776, 1985).

Other oncoproteins are also thought to be involved in gene regulation. For example, the nuclear-localized oncogene product of v-jun (viral jun) binds to specific sites on DNA (Struhl, K., *Cell* 50:841–846, 1987) and is homologous to the c-jun (cellular jun) product, which also binds specific sites on DNA. The jun gene product appears to be identical to the previously characterized transcription factor AP-1 (Bohmann, D. et al. *Science* 238:1386–1392, 1987).

It is desirable to identify compounds that inhibit oncoprotein activity. By inhibiting oncoprotein activity, inhibition and/or control of oncoprotein-induced cell growth may be achieved. Especially, it is desirable to identify inhibitors of oncoproteins that do not alter the activity of the normal cellular equivalents of the oncoproteins. Administration of such inhibitors would provide therapeutic benefits in the treatment of diseases in which expression and activity of the oncoprotein is a factor in promoting cell growth or in maintaining the cell in a transformed state.

However, to date, very few oncoprotein inhibitors have been identified. The identification of such inhibitors has suffered for lack of a simple, inexpensive and reliable screening assay that could rapidly identify potential inhibitors and active derivatives thereof. The present invention provides such an assay. Using the instant assay, inhibitors of oncoprotein activity can be identified and, if desired, those inhibitors further screened to eliminate ones which generally inhibit normal cellular transcription or which inhibit activity of the normal cellular oncoprotein homologs.

SUMMARY OF THE INVENTION

Recognizing the importance that inhibitors of oncoproteins would play in the therapeutic treatment of many forms of cancer, and cognizant of the lack of a simple assay system in which such inhibitors might be identified, the inventors have investigated the use of chimeric oncogene constructs in in vivo assays in eukaryotic hosts as a model system in which to identify agents that alter oncogene expression. These. efforts have culminated in the development of a simple, inexpensive assay that can be used to detect inhibitors of the biological activity of mammalian oncoproteins.

The invention provides a quick, reliable and accurate method for objectively identifying compounds, including human pharmaceuticals, as inhibitors of oncoprotein activity and thus as anti-cancer therapeutics.

The invention further provides a method for identifying and classifying the mechanism of action of a bioactive oncoprotein-inhibiting compound.

The invention further provides an assay for monitoring the isolation and/or purification of an oncoprotein-inhibiting compound or mixture of such compounds from a crude preparation.

The invention further provides a method for identifying and classifying a compound as an inhibitor of oncoprotein activity by determining the ability of such a compound to alter expression of a reporter gene, wherein the expression of the reporter gene is operably-linked to the transcriptional regulatory activity of a fusion oncoprotein. The method generally involves: (a) providing a host cell which contains a reporter gene operably-linked to a DNA binding site and which contains an oncoprotein fusion gene which expresses an oncoprotein fusion capable of binding to the DNA binding site (such that the expression of the reporter gene is mediated by the DNA bound oncoprotein fusion); (b) contacting the host cell with the compound; and (c) assaying expression of the reporter gene. A decrease in reporter gene expression is indicative of a compound which inhibits oncoprotein activity.

The invention further provides a method for identifying the ability of a compound to inhibit oncoprotein activity by determining the compound's ability to inhibit oncoprotein-induced expression of a reporter molecule, the method comprising (a) growing a first host in the presence of a compound wherein the first host has been transformed with one or more recombinant constructs encoding a fusion protein and a reporter gene and wherein expression of a reporter gene is operably-linked to expression of the fusion protein, (b) growing a second host in the presence of the same compound wherein the second host has been transformed with one or more recombinant constructs encoding a fusion oncoprotein and a reporter gene and wherein expression of the reporter gene is operably-linked to expression of the fusion oncoprotein; and (c) comparing expression of such reporter gene in the first host with expression of such reporter gene in the second host.

In preferred embodiments, the host utilized for the methods of the invention are yeast or cultured animal cells.

DESCRIPTION OF THE PREFERRED EMBODIMENTS

In the description that follows, a number of terms used in recombinant DNA technology are utilized. In order to provide a clearer and consistent understanding of the specification and claims, including the scope to be given such terms, the following definitions are provided.

Operably-linked. As used herein, operably-linked means that two macromolecular elements are arranged such that modulating the activity of the first element induces an effect on the second element. In this manner, modulation of the activity of a promoter element may be used to alter and/or regulate the expression of an operably-linked coding sequence. For example, the transcription of a coding sequence that is operably-linked to a promoter element is induced by factors that "activate" the promoter's activity; transcription of a coding sequence that is operably-linked to a promoter element is inhibited by factors that "repress" the promoter's activity. Thus, a promoter region is operably-linked to the coding sequence of a protein if transcription of such coding sequence activity is influenced by the activity of the promoter.

Fusion construct. The term "fusion construct" refers generally to recombinant genes which encode fusion proteins and fusion oncoproteins.

Fusion protein. A fusion protein is a hybrid protein. A hybrid protein is a protein which has been constructed to contain domains from at least two different proteins. As used herein, by "fusion protein" is meant a hybrid protein which possesses (a) a transcriptional regulatory domain from a transcriptional regulatory protein other than an oncoprotein, and (b) a DNA binding domain from a DNA binding protein. The structure of the fusion protein is such that the transcriptional regulatory domain and the DNA binding domain are arranged in a manner that allows both domains to be biologically active. The protein that is the source of the transcriptional regulatory domain is different from the protein that is the source of the DNA binding domain, that is, the two domains are heterologous to each other.

The transcriptional regulatory domain of the fusion protein may either activate or repress transcription of target genes, depending on the native biological activity of the domain. As used herein, the term "fusion protein" is not meant to include the fusion oncoproteins of the invention as described herein below.

The term "fusion protein gene" is meant to refer to a DNA sequence which codes for a fusion protein. A fusion protein gene may further provide transcriptional and translational regulatory elements for the transcriptional and translational control thereof.

Fusion Oncoprotein. As used herein, a "fusion oncoprotein" is also a hybrid protein which has been constructed to contain domains from two different proteins. As used herein, by "fusion oncoprotein" is meant a hybrid protein which possesses (a) transcriptional regulatory domain from a transcriptional regulatory oncoprotein, and (b) a DNA binding domain from a DNA binding protein. The structure of the fusion oncoprotein is such that the transcriptional regulatory domain and the DNA binding domain are arranged in a manner that allows both domains to be biologically active. The oncoprotein that is the source of the transcriptional regulatory domain is different from the protein which is the source of the DNA binding domain, that is, the two domains are heterologous to each other.

The transcriptional regulatory domain of the fusion oncoprotein may either activate or repress transcription of target genes, depending on the native biological activity of the domain.

The term "fusion oncoprotein gene" is meant to refer to a DNA sequence which codes for a fusion oncoprotein. A fusion oncoprotein gene may further provide transcriptional and translational regulatory elements for the transcriptional and translational control thereof.

Variant. As used herein, a "variant" of a proteinaceous entity such a fusion protein or a fusion oncoprotein is meant to refer to a proteinaceous entity which contains an amino acid sequence which is substantially similar to, but not identical to, the amino acid sequence of a fusion protein or fusion oncoprotein constructed from naturally-occurring domains.

By a "substantially similar" amino acid sequence is meant an amino acid sequence which is highly homologous to, but not identical to, the amino acid sequence found in a fusion protein or fusion oncoprotein. Highly homologous amino acid sequences include sequences of 80% or more similarity, and possibly lower homology, especially if the homology is concentrated in domains of interest and the similarity is necessary for the function of the protein.

Functional Derivative. As used herein, a "functional derivative" of a fusion protein or fusion oncoprotein is a protein which possesses a biological activity that is substantially similar to the biological activity of the fusion oncoprotein constructs of the invention. By "substantially similar" is meant a biological activity that is qualitatively similar but quantitatively different. For example, a functional derivative of a fusion oncoprotein might recognize the same target as the fusion oncoprotein, but not with the same affinity. In a similar manner, a functional derivative of a fusion protein might recognize the same target as the fusion protein, but not with the same affinity.

As used herein, for example, a peptide is said to be a "functional derivative" when it contains the amino acid backbone of the hybrid protein of the invention plus additional chemical moieties not usually a part of the hybrid protein. Such moieties may improve the derivative's solubility, absorption, biological half-life, etc. The moieties may alternatively decrease the toxicity of the derivative, or eliminate or attenuate any undesirable side effect of the derivative, etc. Moieties capable of mediating such effects are disclosed in *Remington's Pharmaceutical Sciences* (1980). Procedures for coupling such moieties to a molecule are well known in the art.

A functional derivative of hybrid protein may or may not contain post-translational modifications such as covalently linked carbohydrate, depending on the necessity of such modifications for the performance of the methods of the invention.

The term "functional derivative" is intended to encompass functional "fragments," "variants," "analogues," or "chemical derivatives" of a molecule.

Response. As used herein, the term "response" is intended to refer to a change in any parameter that can be used to measure and describe the effect of a compound on the activity of an oncoprotein or a fusion oncoprotein of the invention. The response may be revealed as a physical change (such as a change in the phenotype) or, it may be revealed as a molecular change (such as a change in a reaction rate or affinity constant). Detection of the response may be performed by any means appropriate.

Compound. As used herein, the term "compound" is intended to refer to a chemical entity, whether in the solid, liquid, or gaseous phase. The term should be read to include synthetic compounds, natural products and macromolecular entities such as polypeptides, polynucleotides, or lipids, and also small entities such as neurotransmitters, ligands, hormones or elemental compounds.

Bioactive Compound. As used herein, the term "bioactive compound" is intended to refer to any compound that induces a measurable response in the assays of the invention.

Promoter. As used herein, a "promoter" is a DNA sequence located proximal to the start of transcription at the 5' end of an operably linked transcribed sequence. The promoter may contain one or more regulatory elements or modules which interact in modulating transcription of the operably-linked gene.

Expression. As used herein, expression is the process by which the information encoded within a gene is revealed. If the gene encodes a protein, expression involves both transcription of the DNA into mRNA, the processing of mRNA (if necessary) into a mature mRNA produce, and translation of the mature mRNA into protein.

A nucleic acid molecule, such as a DNA or gene is said to be "capable of expressing" a polypeptide if the molecule contains the coding sequences for the polypeptide and the expression control sequences which, in the appropriate host environment, provide the ability to transcribe, process and translate the genetic information contained in the DNA into a protein product, and if such expression control sequences are operably-linked to the nucleotide sequence that encodes the polypeptide.

Cloning vehicle. As used herein, a "cloning vehicle" is any molecular entity that is capable of delivering a nucleic acid sequence into a host cell for cloning purposes. Examples of cloning vehicles include plasmids or phages, including those which can replicate autonomously in the host cell. Alternatively, a nucleic acid molecule that can insert (integrate) into the host cell's chromosomal DNA is also useful, especially a molecule which inserts into the host cell's chromosomal DNA in the stable manner, that is, a manner which allows such molecule to be inherited by daughter cells.

Cloning vehicles are often characterized by one or a small number of endonuclease recognition sites at which such DNA sequences may be cut in a determinable fashion without loss of an essential biological function of the vehicle, and into which DNA may be spliced in order to bring about its replication and cloning.

The cloning vehicle may further contain a marker suitable for use in the identification of cells transformed with the cloning vehicle. For example, a marker gene, may be a gene which confers resistance to a specific antibiotic on a host cell. The word "vector" is sometimes used for "cloning vehicle."

Expression vehicle. As used herein, an "expression vehicle" is a vehicle or vector similar to the cloning vehicle but is especially designed to provide an environment which allows the expression of the cloned gene after transformation into the host. One manner of providing such an environment is to provide transcriptional and translational regulatory sequences on such expression vehicle, such transcriptional and translational regulatory sequences being capable of being operably linked to the cloned gene. Another manner of providing such an environment is to provide a cloning site or sites on such vehicle, wherein a desired cloned gene and desired expression regulatory elements may be cloned.

In an expression vehicle, the gene to be cloned is usually operably-linked to certain control sequences such as promoter sequences. Expression control sequences will vary depending on whether the vector is designed to express the operably-linked gene in a prokaryotic or eukaryotic host and may additionally contain transcriptional elements such as enhancer elements, termination sequences, tissue-specificity elements, and/or translational initiation and termination sites.

Host. As used herein, by "host" is meant any organism that is the recipient of a cloning or expression vehicle. In preferred embodiments, the host of the invention is a yeast cell or a cultured animal cell such as a mammalian or insect cell. In an especially preferred embodiment, the yeast host is *Saccharomyces cerevisiae*. In another especially preferred embodiment, the mammalian host is a cultured CV-1 or NIH3T3 cell.

In general, proteins that regulate transcription possess an ability to bind specific DNA sequences and an ability to regulate specific promoters which contain those sequences. Such proteins generally possess at least two functions, a DNA binding function and a transcriptional regulatory function. Upon binding to DNA, the transcriptional regulatory domain of the protein alters (activates or represses) transcription of the gene operably-linked to the regulatory protein's DNA binding site.

In many DNA-binding regulatory proteins, the DNA binding function and the transcription regulatory function are carried on separable domains. These domains are often discrete units and located at sites in the amino acid chain that can be separated physically. By separating these units, it is possible to construct derivatives of native DNA-binding regulatory proteins. Such derivatives may, for example, possess the ability to bind DNA but not the ability to regulate transcription of DNA. Further, such derivatives may be DNA binding domain of one regulatory protein and the transcriptional regulatory domain of another regulatory protein.

According to the invention, by combining domains from two different proteins in a single "fusion" protein, there may be created one protein that possesses the combined properties of the original domains; such protein may be used to identify and characterize compounds or other factors that modulate or otherwise alter the activity of one of the fused domains.

For use in the methods of the invention, a host must possess at least two genetic constructs; a first construct providing genetic sequences capable of expressing either a fusion protein or a fusion oncoprotein; and, a second construct providing genetic sequences containing a reporter gene. In such a host cell, it is necessary that the promoter of the reporter gene contains the DNA binding element that is recognized by the DNA binding domain of the fusion protein or fusion oncoprotein. Thus, expression (or repression) of the synthesis of the reporter gene is dependent upon expression and binding of the fusion protein or fusion oncoprotein to the reporter gene's promoter.

Preferably, two hosts are utilized in the methods of the invention. One host possesses a fusion protein construct, the other host contains a fusion oncoprotein construct, and both hosts contain the same reporter gene construct. Further, the DNA binding domain in the fusion protein construct in the first host is preferably the same as the DNA binding domain in the fusion oncoprotein construct. By exposing both hosts to a compound and comparing the expression of the reporter in the two hosts, the ability of a compound to specifically alter oncogene-induced transcription (and not alter transcription in general) may be determined.

The transcriptional regulatory domain of the fusion protein construct in the first host may be any domain sufficient to permit regulation, and preferably activation, of transcription. For example, the normal cellular counterpart of the oncoprotein transcriptional regulatory domain used in the fusion oncoprotein construct in the second host may be used. Alternatively, and especially when the oncoprotein's normal cellular counterpart is either unidentified or identical to the oncoprotein, the transcriptional regulatory domain from a different transcriptional regulatory protein may be used. Use of the transcriptional regulatory domain of a different regulatory protein may also be advantageous, if desired, to ensure that any potential inhibitors which are identified do not inhibit transcription in general.

The methods of the invention may be used for the identification of compounds that inhibit transcription per se. The methods of the invention may also be used for the identification of compounds that inhibit or otherwise interfere with protein oligomerization, especially if such oligomerization is necessary for transcriptional regulation of a marker gene. Without intending to be limited to a specific mechanism of action of the bioactive compounds identified by the methods of the invention, it is known that the transcriptional regulatory domain of many DNA binding proteins may interact with (oligomerizes with) a second, non-DNA-binding protein and, in the oligomer form, stimulate transcription of operably-linked genes. Accordingly, in those fusion constructs of the invention which require such oligomerization for transcriptional activity, compounds that inhibit such oligomerization also inhibit oncoprotein activity.

Any DNA binding protein or transcriptional regulatory protein, and especially eukaryotic proteins may be used as a source of a desired domain in the fusion protein and fusion oncoprotein constructs of the invention. Many transcriptional regulatory proteins are known. Transcriptional regulatory proteins, and the methods used to characterize the domains of such proteins, have been reviewed by Johnson and McKnight, *Annu. Rev. Bioch.* 58:799–839, 1989, incorporated herein by reference.

In the constructs of the invention, the sequences that provide (1) the DNA binding domain and (2) the DNA binding element recognized by that domain may each be homologous to a host cell or heterologous to the host cell. Preferably, a heterologous DNA binding domain and element are used. In an especially preferred embodiment, in eukaryotic hosts, the source of the DNA binding element, and the source of the DNA binding domain of the protein that binds that element, is prokaryotic. Use of prokaryotic regulatory elements with a eukaryotic host in the methods of the invention is advantageous as it greatly diminishes the possibility that the host will contain an endogenous element which may titer, dilute or otherwise interfere with interpretation of the results provided by the methods of the invention.

While not necessary for the practice of the methods of the invention, when the transcriptional regulatory domain chosen is not that of the normal cellular counterpart of the oncoprotein (for example, the corresponding c-Myc domain of v-Myc), it may be desirable to utilize a DNA transcriptional regulatory domain from a DNA regulatory protein that is in the same DNA binding class as the oncoprotein. Many regulatory proteins that share homologies in their DNA binding sites may also share similarities in the manner in which they regulate transcription.

Two characteristic DNA binding motifs are the helix-turn-helix motif and the zinc finger motif. The following proteins contain a zinc finger motif: the yeast proteins GAL4, HAP1, ADR1, SWI5, ARGRII and LAC9, the Neurospora protein cys-3, the Drosophila proteins kruppel, snail, hunchback, serendipity, and suppressor of hairy wing, and the vertebrate proteins Sp1, H2TF-1/NF-$_K$B-like protein, PRDI, TDF, GLI, Evi-1, the glucocorticoid receptor, the estrogen receptor, the progesterone receptor, the thyroid hormone receptor (C-erbA) and ZIF/268. The following proteins contain a helix-turn-helix motif: the yeast mating type factors MATα1, MATa2 and MATa1, the Drosophila proteins antennapedia, ultrabithorax, paired, fushi tarazu, cut, and engrailed, and the vertebrate proteins OTF-1(OCT1), OTF-2(OCT2) and PIT-1.

Transcriptional regulatory domains preferred in the methods of the invention are those of GCN4 and GAL4.

Examples of prokaryotic DNA binding proteins with DNA binding domains and DNA binding elements useful in the methods of the invention include LexA, CAP (catabolite activator protein of *E. coli*), the bacteriophage λ CRO and CI proteins, lac repressor, trp repressor, gal repressor, and phage 434 and P22 repressor and Cro proteins. In addition, any of the DNA binding domains from the DNA regulatory proteins listed previously may be used if enough molecules of the protein are present in the cell to titer any homologous DNA binding site that is present in the host cell.

The identification of a DNA binding domain in a protein may be performed by a variety of techniques known in the art and previously used to identify such domains. DNA binding proteins, and DNA binding domains in such proteins, are identified and purified by their affinity for DNA. For example, DNA binding may be revealed in filter hybridization experiments in which the protein (usually labelled to facilitate detection) is allowed to bind to DNA immobilized on a filter or, vice versa, in which the DNA binding site (usually labelled) is bound to a filter upon which the protein has been immobilized. The sequence specificity and affinity of such binding is revealed with DNA protection assays and gel retardation assays. Purification of such proteins may be performed utilizing sequence-specific DNA affinity chromatography techniques, that is, column chromatography with a resin derivatized with the DNA to which the domain binds. Proteolytic degradation of DNA binding proteins may be used to reveal the domain that retains the DNA binding ability.

The DNA binding domain is engineered into the fusion oncoprotein in a manner that does not destroy the ability of the domain to recognize the DNA element to which it naturally binds; that is, the DNA binding domain is provided in a manner that does not destroy the DNA binding specificity of the DNA binding domain.

Transcriptional regulatory domains in proteins may also be identified by techniques known in the art, and preferably using a cloned protein in which the genetic sequences may be easily manipulated. In a cloned form, synthesis of derivatives of the native protein is preferably directed by expression vectors so that the transcriptional regulatory domain may be identified by monitoring the ability of the expressed derivatives to activate transcription of genes known to be activated by the full-length protein. In addition, cell-free transcription assays capable of accurate transcription from the desired promoter may be performed using cloned DNA templates.

The fusion protein and fusion oncoprotein of the invention may contain more than one transcriptional activation domain. In a similar manner, the promoter region of the reporter gene may contain more than one DNA binding element each of which are capable of altering (inducing and/or inhibiting) expression of the operably linked reporter gene.

The genetic constructs of the invention (fusion protein and reporter gene or fusion oncoprotein and reporter gene) may be placed on two different plasmids or fragments of recombinant DNA, or combined on one plasmid or fragment of recombinant DNA. The constructs may also be inserted into the genome of a host cell.

Preferably, the fusion oncoprotein is engineered such that the native DNA binding domain of the oncoprotein (if any) has been removed (or inactivated) and replaced with a heterologous DNA binding domain. As a result, the fusion oncoprotein no longer binds to any specific DNA elements that may be natural targets of the oncoprotein. Rather, the fusion oncoprotein now specifically binds to the DNA sequence recognized by the heterologous DNA binding domain on the fusion oncoprotein. Once bound to DNA, transcription of operably-linked genes occurs.

In another embodiment, the fusion oncoprotein retains its native DNA binding domain but also contains a second heterologous DNA binding domain. In this embodiment, the fusion oncoprotein may still bind to any specific DNA elements that are normally targets of the oncoprotein so long as binding of the protein to its native sites does not preclude its binding to the heterologous DNA binding element.

The fusion constructs may also lack a native dimerization domain. In certain cases, the presence of the native dimerization domain compromises activation through LexA operators, either by preventing dimerization of the LexA DNA binding domains (and hence preventing the fusion protein from binding a LexA operator) or by facilitating a heterodimeric interaction with some other cellular protein (e.g., another transcription factor or the nuclear matrix) and thus reducing the number of fusion protein molecules available for homodimerization and target promoter binding. Dimerization domains of the proteins and oncoproteins of the invention may be removed from the DNA sequence encoding an oncoprotein or other protein by enzymatic digestion (e.g., restriction digestion) or, if the dimerization domain is carboxy-terminal, by insertion of a stop codon upstream of or within the domain.

The reporter gene may be any gene whose expression can be monitored and whose expression may serve as an indicator of fusion protein or fusion oncoprotein activity. In a preferred embodiment, the reporter gene is a gene not normally expressed by the host, or is a gene that replaces a gene endogenous to the host.

The product of the reporter gene may be directly assayed with an immunoassay. Such immunoassays include those wherein the antibody is in a liquid phase or bound to a solid phase carrier. In addition, the reporter gene can be detectably labeled in various ways for use in immunoassays. The preferred immunoassays for detecting a reporter protein using the include radioimmunoassays, enzyme-linked immunosorbent assays (ELISA), or other assays known in the art, such as immunofluorescent assays, chemiluminescent assays, or bioluminescent assays.

Any detectable phenotypic change,may serve as the basis for the methods of the invention. Especially useful are reporter genes that confer a new phenotype on the host when expressed. Genes that endow the host with an ability to grow on a selective medium are especially useful. For example, in yeast, use of the yeast LEU2 gene as a reporter gene in mutant strains that lack endogenous LEU2 activity allows such yeast to grow on leucine as a sole carbon source (see, e.g., *The Molecular Biology of the Yeast Saccharomyces*, ed. Strathern et al., Cold Spring harbor Press, Cold Spring Harbor, N.Y., 1981; and the methods described in Rothstein et al., *Mol. Cell Biol.* 7:1198, 1987). Expression of the reporter gene is monitored by merely observing whether the host retains the ability to grow on leucine.

The *E. coli* lacZ gene is also very useful as a reporter. In hosts which utilize the lacZ gene as a reporter gene, expression and activity of the fusion oncoprotein can be easily scored by monitoring the production of β-galactosidase. The production of β-galactosidase may be visually monitored in the presence of the chromophoric dye, X-gal, that turns blue after hydrolysis by the enzyme.

Other reporter genes include his3, ura3, trp1 and, an especially preferred reporter gene in mammalian cells, chloramphenicol acetyltransferase (CAT).

One of ordinary skill in the art can imagine many other appropriate reporter systems that would reveal the presence or inhibition of biological activity of the fusion oncoprotein.

That the effect of a desired compound is due to an effect on transcription and not an effect on the activity of the reporter product per se can be established by comparing the effect of such a compound in hosts containing the oncoprotein fusion product with the effects of such a compound in hosts containing a non-oncoprotein fusion product, if both hosts contain the same reporter gene construct.

In a preferred embodiment of the methods of the invention, the fusion oncoprotein gene contains a sequence coding for the bacterial repressor protein LexA and a sequence coding for the transcription activation domain of the viral oncoprotein, vFos. Expression of such a gene results in the fusion oncoprotein "LexA-vFos." LexA-vFos retains the ability to bind to the LexA DNA binding element. LexA-vFos also retains the potential to activate transcription due to the presence of the vFos transcriptional activation domain. Binding of the LexA-vFos fusion oncoprotein results in activation of transcription due to the presence of an activating domain or domains carried on the vFos moiety.

Reporter constructs in which the LexA "repressor-operator" sequence (the DNA binding element recognized by the LexA DNA binding domain) is a module or element with a promotor that itself is operably-linked to a lacZ reporter gene will express the lacZ gene product in response to binding of a LexA-vFos fusion oncoprotein. A compound that alters the activity of the fusion oncoprotein is readily identified by evaluating the ability of the hosts to express the lacZ reporter gene and thus hydrolyze X-gal to the blue chromophore. When oncoprotein activity is altered by the presence of a compound which inhibits such activity, the host cell alters the expression of the lacZ reporter gene and thus alter its ability to hydrolyze X-gal to the blue chromophore.

When yeast are used as hosts in the methods of the invention, the yeast strains may be separately plated and grown as lawns. A compound which is to be tested may be applied to one of the plates on a filter paper disk that is impregnated with such compound, or alternatively be incorporated into the media upon which the yeast are growing. The ability of a compound to alter oncoprotein-induced transcription activation activity may be detected by the appearance of a "zone" around the compound-impregnated disk. For example, if the compound is toxic to yeast survival, the yeast will not grow in the zone containing the compound.

When animal cells in culture are used as the host cells, a compound which is to be tested may be added to the culture medium.

The permeability of cells to various compounds may be enhanced, if necessary, by use of a mutant cell strain that possess an enhanced permeability or by using compounds that are known to increase permeability. For example, in yeast, compounds such as polymyxin B nonapeptide may be used to increase the yeast's permeability to small organic compounds. In cells from higher eukaryotes, DMSO may be used to increase permeability. Analogs of such compounds that are more permeable across yeast membranes may also be used. For example, a dibutyryl derivative of a compound often provides an enhanced permeability of the compound to biological membranes.

The methods of the invention may be used for the identification of bioactive compounds that interfere with membrane-associated and/or with cytoplasmically-localized oncoprotein activity. For example, the oncoproteins Ras and Src stimulate Fos-dependent gene expression in eukaryotic cells. By assaying for a bioactive compound which alters a marker of such expression, bioactive compounds that inhibit Ras or Src stimulation of Fos-dependent transcription may be identified.

In a similar manner, the methods of the invention can be used to identify inhibitors of protein kinases, for example, when the activity of such a kinase ultimately alters the transcription of a marker gene according to the methods of the invention.

The DNA sequence of the fusion protein and/or target gene may be chemically constructed if it is not desired to utilize a clone of the genome or mRNA as the source of the genetic information. Methods of chemically synthesizing DNA are well known in the art and may be performed by a commercial vendor.

To express the recombinant fusion constructs of the invention, transcriptional and translational signals recognizable by the host are necessary. A cloned fusion protein or cloned oncoprotein encoding sequence, obtained through the methods described above, may be operably-linked to sequences controlling transcriptional expression in an expression vector, and introduced, for example by transformation, into a host cell to produce the recombinant fusion proteins, or fusion oncoproteins, or functional derivatives thereof, for use in the methods of the invention.

Transcriptional initiation regulatory signals can be selected that allow for repression or activation of the expression of the fusion construct, so that expression of the fusion construct can be modulated, if desired. Of interest are regulatory signals that are temperature-sensitive so that by varying the temperature, expression can be repressed or initiated, or that are subject to chemical regulation, for example, by a metabolite or a metabolite analog added to the growth medium.

Alternatively, the fusion construct may be constitutively expressed in the host cell.

Where the native expression control sequences do not function satisfactorily in the host cell, then sequences functional in the host cell may be substituted.

Expression of the fusion constructs in different hosts may result in different post-translational modifications which may alter the properties of the proteins expressed by these constructs. It is necessary to express the proteins in a host wherein the ability of the protein to retain its biological function is not hindered. Expression of proteins in yeast hosts is preferably achieved using yeast regulatory signals. The vectors of the invention may contain operably-linked regulatory elements such as enhancer elements (upstream activator sequences in yeast), or DNA elements which confer species, tissue or cell-type specific expression on an operably-lined gene.

In general, expression vectors containing transcriptional regulatory sequences, such as promoter sequences and transcription termination sequences, are used in connection with a host. These sequences facilitate the efficient transcription of the gene fragment operably-linked to them. In addition, expression vectors also typically contain discrete DNA elements such as, for example, (a) an origin of replication which allows for autonomous replication of the vector, or, elements which promote insertion of the vector into the host's chromosome in a stable manner, and (b) specific genes which are capable of providing phenotypic selection in transformed cells. Eukaryotic expression vectors may also contain elements which allow it to be maintained in prokaryotic hosts; such vectors are known as shuttle vectors.

The precise nature of the regulatory regions needed for gene expression will vary between species or cell types and there are many appropriate expression vector systems that are commercially available.

In a highly preferred embodiment, yeast are used as the host cells. The elements necessary for transcriptional expression of a gene in yeast have been recently reviewed (Struhl, L. *Ann. Rev. Biochem.* 58:1051–1077 (1989), incorporated herein by reference). In yeast, most promoters contain three basic DNA elements: (1) an upstream activator sequence (UAS); (2) a TATA element; and, (3) an initiation (I) element. Some promoters also contain operator elements.

In another embodiment, mammalian cells are used as the host cells. A wide variety of transcriptional and translational regulatory signals can be derived for expression of proteins in mammalian cells and especially from the genomic sequences of viruses which infect eukaryotic cells.

Once the vector or DNA sequence containing the construct(s) is prepared for expression, the DNA construct(s) is introduced into an appropriate host cell by any of a variety of suitable means, for example by transformation. After the introduction of the vector, recipient cells are grown in a selective medium, which selects for the growth of vector-containing cells. Expression of the cloned gene sequence(s) results in the production of the fusion protein or in the production of a fragment of this peptide. This expression can take place in a continuous manner in the transformed cells, or may be induced by exogenous agents (supra).

Preferably, genetically stable transformants are constructed by integrating the fusion protein DNA into the chromosome of the host. Such integration may occur unassisted following transformation with the exogenous DNA, or it may depend upon a vector that functionally inserts itself into the host chromosome, for example, using retroviral vectors, transposons or other DNA elements that promote integration of DNA sequences in chromosomes. Alternatively, the fusion gene may be introduced on a vector which does not replicate; expression of the fusion protein continues so long as the vector persists in the cell population.

Cells that have been transformed with the fusion protein DNA vectors of the invention are selected by also introducing one or more markers that allow for selection of host cells that contain the vector, for example, the marker may provide an amino acid synthetic enzyme or biocide resistance, e.g., resistance to antibiotics, such as G418, or heavy metals, such as copper, or the like.

In preferred embodiments, *Saccharomyces cerevisiae* is the preferred yeast host and CV-1 cells or NIH3T3 cells are the preferred mammalian cell hosts.

The methods of the invention provide a rapid, reliable and economic manner in which to screen and classify compounds as inhibitors of oncoprotein activity. The methods of the invention are amenable to large scale industrial screening of large numbers of compounds or preparations for oncoprotein inhibitor activity. In addition, the methods of the invention allow the screening of any pure compound, mixture of compounds, or mixture of preparations, so as to identify the additive, synergistic, or detrimental effects of such compositions. The methods of the invention are also useful for the identification of the presence of bioactive compounds in crude extracts, and as assays for the purification of bioactive compounds therefrom. The methods of the invention are also useful in the evaluation of the stability of the bioactive compounds identified as above, and, especially, for the evaluation of the efficacy of various preparations.

The following examples further describe the materials and methods used in carrying out the invention. The examples are not intended to limit the invention in any manner.

EXAMPLES

There now follow examples of assays and oncoprotein fusions useful in the invention. These examples are provided to illustrate, not limit, the invention.

Example 1

Construction of Fusion Genes and Fusion Oncogenes a. Generally

The construction of LexA fusion genes is described in Lech, K., et al., Cell 52:179–184, 1988; Brent and Ptashne, *Cell* 43:729, 1985; and Brent, U.S. Pat. No. 4,833,080, hereby incorporated by reference. Also described in Brent, U.S. Pat. No. 4,833,080, are plasmid vectors which may be used to construct LexA fusion genes generally (e.g., pRB500), yeast expression vectors (e.g., pAAH5), and yeast target (or reporter) plasmids which include yeast target genes carrying upstream LexA operators.

b. LexA-Gal4

The construction of LexA-Gal4 fusion genes is described in Brent, U.S. Pat. No. 4,833,080.

c. LexA-vMyc

Plasmid MC38, containing the entire avian MC29 avian myelocytomatosis virus (Reddy, E. P. et al., *Proc. Natl. Acad. Sci. U.S.A.* 80:2500–2504, 1983; available from the American Type Culture Collection, Rockville, Md., ATCC Accession Number 41007) was cut at an SspI site downstream of the viral gag-myc gene. The mixture was treated with T4 DNA ligase in the presence of HindIII linkers, and the ligation mixture treated with PstI and HindIII. The PstI-HindIII piece that contained most of the myc gene was isolated and inserted into PstI-HindIII cut pUC18 to generate pKA58. In a separate series of constructions, a BamHI-XmnI piece from pRB480 (Brent, R. et al., *Nature* 312:612–615, 1984; Brent, U.S. Pat. No. 4,833,080), which encoded the amino terminal portion of LexA, was ligated to a double-stranded adaptor of the sequence

CGGGGAGCTGCA

GCCCCTCG and the resulting fragment was inserted into BamHI-PstI cut pUC19 to yield the plasmid pKA144. BamHI cuts in the tetracycline gene of pRB480 and pBR322. The BamHI-PstI LexA piece from pKA144, the PstI-HindIII v-myc piece from pKA58, and the HindIII-BamHI piece from pBR322 were ligated together to generate pKA210. Plasmid DNA was screened from bacterial colonies on tetracycline-containing LB plates. One such plasmid, pKA210, contains the first 87 codons of lexA, three codons contributed by the adaptor fragment, and codons 51 to 425 of v-myc. The fusion gene encodes a 465 amino acid protein whose sequence across the fusion junction is pro gly glu leu gln pro, where pro is amino acid 87 of LexA and gln is amino acid 51 of native vMyc protein. This gene codes for a fusion protein with a predicted molecular weight of approximately 51,000 Daltons.

Alternatively, a LexA-vMyc fusion protein may be constructed which lacks its dimerization domain (i.e., lacks its helix-loop-helix domain and leucine zipper domain). Such a construct was produced as follows. pKA58 (supra) was digested with BamHI and PstI (enzymes which cleave pKA58 within its polylinker) and a series of four synthetic oligonucleotides were inserted into this site to recreate the complete (native) N-terminal vMyc sequence. The resultant plasmid was termed BHvMyc. An EcoRI-HindIII fragment containing the pUC18 polylinker and the LexA-vMyc gene was excised from BHvMyc and inserted into an EcoRI/HindIII-digested Lex202PL backbone (Ma and Ptashne, Cell 51:113, 1987; Ruden et al., *Nature* 350:250, 1991); Lex202PL is a plasmid which contains amino acids 1-202 of LexA, including the LexA dimerization domain. The resultant plasmid, termed H202/vMyc, contained amino acids 1-202 of LexA fused in frame to amino acids 1-425 of vMyc. To delete the Myc dimerization domain, H202/vMyc was digested with BalI at a unique site corresponding to amino acid 362 in the Myc protein. A polylinker containing a 3-frame stop codon (New England Biolabs linker #1062, Beverly, Mass.) was inserted at this site to produce a gene which encoded a truncated LexA-vMyc protein; this protein lacked a Myc helix-loop-helix domain and also lacked a Myc leucine zipper. The plasmid was termed H202/vMycΔC. In yeast, the LexA-vMyc protein encoded by H202/vMycΔC was found to activate LexA-containing operator constructs more strongly than Myc fusion proteins which included a dimerization domain. In mammalian cells, the truncated protein provided a measurable level of MyC activity; Myc fusion constructs which included a native Myc dimerization domain did not.

d. LexA-cMyo

Plasmid pCDEM5.8 (a gift of Adrian Hayday), containing human c-myc cDNA, was digested with SmaI and BamHI and a 2300 base pair fragment, including exons 2 and 3 of the c-myc gene, were ligated to the SmaI-BamHI fragment of pUC19 to generate pC20. This plasmid was then partially digested with PstI and a fragment containing all but the first 38 codons of the c-myc gene was isolated and ligated to PstI cut pKA1035, a plasmid identical to pKA144 except that the SinaI site in the pUC19 backbone was destroyed by cutting at an overlapping KpnI site and chewing back the overhang with T4 DNA polymerase. A resulting plasmid, pVR103, contained the first 87 codons of lexA, three codons contributed by the adaptor fragment, and codons 39 through 440 of c-myc. The fusion gene encodes a 492 amino acid protein whose sequence across the fusion junction is pro gly glu leu gln pro, where pro is amino acid 87 of LexA and gln is amino acid 39 of native cMyc protein. This gene codes for a fusion protein with a predicted molecular weight of approximately 54,000 Daltons. The human c-myc gene is also available from the American Type Culture Collection (ATCC Accession No. 39286).

e. LexA-vFos

Plasmid pFBJ-2 contains an FBJ-MuSV provirus in a 5800 bp HindIII fragment inserted into the HindIII site of pBR322 (Van Beverens, C. et al., *Cell* 32:1241–1255, 1983; Curran, T. et al., *Virol.* 116:221–236, 1982; Curran, T. et al., *J. Virol.* 42:114–122, 1982). This plasmid was cut with EagI and filled in the 5' overhand with Klenow. The plasmid was then cut with HindIII and a 3600 bp fragment was isolated that contained the carboxy-terminal portion of the v-fos protein. This v-fos EagI (filled)-HindIII piece was ligated to the lexA BamHI-XmnI piece from pRB480 (below) and to the HindIII-BamHI backbone fragment of pBR322. *E. coli* containing this construction were identified by their tetracycline resistance. A typical resulting plasmid, pKA195, contained the first 87 codons of lexA fused directly to codons 23-381 of v-fos. This fusion gene encodes a 446 amino acid protein whose sequence across the fusion junction is pro ala gly, where pro is amino acid 87 of LexA and the first ala is amino acid 23 of the v-fos product. The v-fos gene may also be obtained from the American Type Culture Collection (ATCC Accession No. 41040).

f. LeKA-cFos

Plasmid FMC5A contains the mouse cFos cDNA in pGEM-1. This plasmid was first cut with EagI and the 5' overhang filled in with Klenow. Next, it was cut with HindIII and a 1900 bp EagI(filled)-HindIII fragment containing the carboxy-terminal fragment of the c-fos gene was ligated to the BamHI-XmnI fragment of pRB481Flip and the HindIII-BamHI fragment of pRB481. pRB481 contains a HindIII-ended LexA gene, including its *E. coli* promoter in the plasmid pi4-8 (Brent and Ptashne, *Cell* 43:729, 1985; Brent, U.S. Pat. No. 4,833,080). In this construction, pRB480 (Brent, U.S. Pat. No. 4,833,080) could have been used in place of pRB481. pRB481Flip was constructed by cutting pRB481 with HindIII and isolating a plasmid whose HindIII-ended LexA fragment was in the opposite orientation. *E. coli* that contained a LexA-cFos fusion gene were identified by their tetracycline resistance. A resulting plasmid, pVR6, contained the first 87 amino acids of LexA fused directly to codons 23 to 380 of c-fos. The fusion gene encodes a 445 amino acid protein whose sequence across the fusion junction is pro ala gly, where pro is amino acid 87 of LexA and ala is amino acid 23 of the c-fos product. This gene codes for a fusion protein with a predicted molecular weight of approximately 49,000 Daltons. The mouse c-fos gene may also be obtained from the American Type Culture Collection (ATCC Accession No. 41041)

g. LexA-vJun

Plasmid pLexA-vJun is described in Struhl, *Nature* 332:649, 1988. The v-jun gene is available from the American Type Culture Collection (ATCC Accession No. 63026).

Example 2

Yeast Plasmids

Generally, the yeast target (or reporter) plasmids carried the $URA3^+$ gene, a 2 μm replicator, and promoter elements as shown in Brent, U.S. Pat. No. 4,833,080, incorporated herein by reference.

To express the LexA-Myc and LexA-Fos fusion constructs in yeast, HindIII-ended fusion genes were inserted into the HindIII site of pAAH5. pAAH5 carried the $LEU2^+$ gene, a portion of the 2μ plasmid to allow replication in yeast, and a DNA fragment containing the ADH1 promoter and transcription terminator flanking the HindIII site (Ammerer, G., *Meth. Emyzmol.* 101:192–210, 1983; Brent, U.S. Pat. No. 4,833,080). Other yeast expression plasmids may be used in place of pAAH5; many are described in Cloning Vectors, ed. Powels et al., Elsevier, 1987.

Alternatively, LexA-vFos may be expressed from plasmids pKL1190NS or pAF3. pKL1190NS was constructed by inserting the BamHI fragment containing the ADH1 promoter, the LexA-vFos gene, and the ADH1 terminator from the pAAH5-LexA-vFos plasmid (above) into pSE358NS. pSE358NS was made by cutting pUN10 (Elledge et al., *Gene* 70:303, 1988) with SalI, digesting the overhanging DNA with Mung Bean Nuclease, and relegating, thus destroying the SalI site. pAF3 was constructed in two steps. First a BamH1/EcoR1-ended fragment from pADE8 (White, J. H., et al., *Nature* 315:350–352 (1985)) that contained the ADE8 gene was inserted into a BamH1/EcoR1-ended pSE358NS backbone to create pA8-7. Next, the BamH1-ended fragment, containing LexA-vFos and the ADH1 promoter and terminator (above), was inserted into pA8-7, producing AF3.

LexA-vJun was expressed and its activity assayed as described in Struhl (*Nature* 332:649, 1988).

Example 3

Mammalian Plasmids

Mammalian target (or reporter plasmids) used herein are described in Godowski, P. J., et al., *Science* 241:812–816, 1988, hereby incorporated by reference. These vectors contain the β-globin promoter fused to the chloramphenicol acetyltransferase gene. One target, OBCO, lacked an upstream LexA operator; the other, XBCO, contained a single LexA operator 125 bp upstream of the startpoint of transcription. Other target plasmids may be constructed by positioning one or more LexA operators (see Brent, U.S. Pat. No. 4,833,080) slightly upstream of a mammalian promoter the activity of which may be assayed.

Expression plasmids coding for the fusion oncoproteins were constructed by respectively inserting the HindIII-ended LexA-vFos or LexA-vMyc gene from pKA195 (Lech, K., et al., *Cell* 52:179–184 (1988)) or H202/vMycΔC into the mammalian expression vector, p6R (Godowski, P. J., et al., *Science* 241:812–816 (1988)). Synthesis of the proteins by these plasmids was directed by the RSV promoter. A number of alternative mammalian expression vectors are described in *Cloning Vectors* (supra).

For expression of LexA-vJun in mammalian cells, pLexA-vJun (supra) was cut at a unique EcoRI site downstream of the LexA-vJun sequence, ligated to an EcoRI-HindIII adaptor, and cleaved with HindIII. The HindIII ended LexA-vJun fragment was first inserted into the HindIII site of pi4-8 (supra) to create pKL8146, and then inserted into the HindIII site of p6R.

Example 4

Experimental procedures a. Bacterial Cell Growth and Transformation

Bacteria were grown and transformed using standard techniques (Ausubel, F. M. et al., *Current Protocols in Molecular Biology*, New York: Green Publishing Associates (1987) and Miller, J., *Experiments in Molecular Genetics*, Cold Spring Harbor Laboratory, Cold Spring Harbor, N.Y. 1972). Plasmid bearing strains were propagated in LB medium containing 100 μg/μl carbenicillin. RB926 (hsdR thiA endA) and JM101 (supE thiA Δ (lac-proAB)/F' traD36 $proA^+$ $proB^+$ $lac7^q$ lacZΔM15) were used as bacterial hosts for plasmid DNA construction.

b. Yeast Microbiological Work

Yeast were grown in YEP medium supplemented with 2% glucose. Transformations were performed as described in Lech, K. et al., *Cell* 52:179–184 (1988). Plasmids were maintained in yeast by growing cells in minimal medium that contained 2% glucose but lacked the nutritional supplement coded for by the plasmid's selectable marker (Sherman, F., et al., *Methods in Yeast Genetics*, Cold Spring Harbor Laboratory, Cold Spring Harbor, N.Y. (1983)). Genes under the control of the GAL10 promoter were induced by growth of host cells for 36 hours on medium that contained 2% galactose.

DBY745 (α ura3 leu2) was used as host in most experiments in yeast (Brent, U.S. Pat. No. 4,833,080). Solid and liquid media used for this purpose were SD medium (lacking uracil) buffered to pH 7.0 by the addition of $N_2HPO_4$ and $KH_2PO_4$ to a 70 mM final concentration. Carbon sources were added to 2% final concentration each.

c. Assay of β-galactosidase Activity

β-galactosidase assays were performed as described in Yocum, R. R. et al., *Mol. Cell. Biol.* 4:1985–1998 (1984), or alternatively were performed on cells grown on solid medium (Lech, K., "Gene Activation by DNA Bound Fos and Myc Proteins," Ph.D. Dissertation, Harvard University, 1990), except that cells to be assayed were grown on solid, rather than in liquid, selective medium. β-galactosidase units were calculated by the equation Units=$1000 \times OD_{420}$/cell volume (ml)×time of reaction (min)×$OD_{600}$.

d. Growth and Transfection of Mammalian Cells

Monkey kidney CV-1 cells (ATCC Accession No. CCL70) were grown in Dulbecco's modified Eagle's medium (DMEM) containing 10% fetal calf serum and split 24 hours before transfection. Transient transfections were performed according to a calcium phosphate precipitation method (Godowski, P. J. et al., *Science* 241:812–816 (1988)). All transfections were repeated at least three times in duplicate to ensure the reproducibility of the results. Typically, 10 μg of fusion protein expression plasmid and 2 μg of target plasmid were introduced into the cells, along with 2.5 μg of a human growth hormone expression plasmid (pXGH5, Selden, R. F. et al., *Mol. Cell. Biol.* 6:3173–3179 (1986); Ausubel, F. M. et al., *Current Protocols in Molecular Biology*, New York: Green Publishing Associates (1987)) as an internal control for transfection efficiency. In those experiments, where the activity of the nuclear oncoprotein (e.g., Fos, Myc, or Jun) is modulated by the activity of a cytoplasmic or membrane-associated oncoprotein (e.g., ras or src), 10 μg of modulator plasmid was also included in the transfection mix. The total amount of DNA was brought up to a total of 25 μg with the control plasmid, pUC18. DNA to be transfected was prepared by two successive cesium chloride gradient centrifugations (Maniatis, T. et al., *Molecular Cloning: A Laboratory Manual*, Cold Spring Harbor Laboratories, Cold Spring Harbor, N.Y. (1982)). Purity and amount of DNAs were determined by agarose gel electrophoresis before and after digestion with restriction enzymes. Human growth hormone expression varied by less than 15% from the average within an experiment and between experiments, indicating that efficiency of transfection remained constant and that cells expressing the oncoproteins were healthy.

The mouse fibroblast line NIH3T3 (ATCC Accession No.CRL 6442) was grown in Dulbecco's modified Eagle's Medium (DMEM) with 10% calf serum using standard procedures. Transfections were carried out using standard calcium precipitation methods (see, e.g., *Current Protocols in Molecular Biology*, supra). Generally, transfections were carried out using 10 μg of LexA-fusion gene-containing plasmid, 2 μg of target plasmid, 2.5 μg XGH5, and 10 μg sheared salmon sperm DNA (as carrier DNA) per 10 cm. plate of cells. Stable transfectants were produced by standard techniques (see, e.g., *Current Protocols in Molecular Biology*, ed. Ausubel et al., New York, 1987) using the above plasmids and 2 μg of a plasmid which confers neomycin resistance (Southern and Berg, *J. Mol. Appl. Genet.* 1:327, 1982), for example, the plasmid pMAMneo (available from Clontech, Palo Alto, Calif.).

e. CAT Assays

Extracts were prepared and CAT assays performed as described in Ausubel, F. M. et al., *Current Protocols in Molecular Biology*, New York: Green Publishing Associates (1987). Protein extracts were diluted so that CAT activity remained in the linear range of enzyme activity versus amount of protein extract. CAT values were determined by excising the $^{14}C$-chloramphenicol spots from a TLC plate and counting them. Percent conversion was calculated by dividing the counts in the acetylated spots by the total of the counts in the acetylated and unacetylated spots and, from this number, deducting the background percent conversion obtained in a parallel mock reaction without protein extract.

Example 5

Identification of an Inhibitor of vFos and/or vMyc in Yeast Cells

Yeast host cells are transformed with plasmids expressing a LexA-vFos fusion oncoprotein (host 'a'), a LexA-vMyc fusion oncoprotein (host 'b'), or a LexA-Gal4 fusion protein (host 'c') as described above. In addition all three yeast strains are cotransformed with a target plasmid (e.g., 1840 or 1027; Brent, U.S. Pat. No. 4,833,080), which contains the coding sequence for β-galactosidase operably-linked to a LexA operator as described above.

A lawn of each of the transformed yeast strains is spread on agar plates containing X-gal in the medium. A small filter disk containing compound W, X, Y, or Z is placed on the lawns. The yeast are allowed to grow, and the plates are monitored for colony growth and colony color by visual observation. Typical results from such an experiment are shown in Table 1.

TABLE 1

Identification of Oncoprotein Inhibitors

| Compound | Yeast | Regulatory Protein | Colony Growth | Color from β-gal Assay with X-gal |
|---|---|---|---|---|
| W | a | LexA-vFos | + | Blue |
|   | b | LexA-vMyc | + | Blue |
|   | c | LexA-Gal4 | + | Blue |
| X | a | LexA-vFos | + | Blue |
|   | b | LexA-vMyc | + | White |
|   | c | LexA-Gal4 | + | White |
| Y | a | LexA-vFos | + | Blue |
|   | b | LexA-vMyc | + | White |
|   | c | LexA-Gal4 | + | Blue |
| Z | a | LexA-vFos | + | White |
|   | b | LexA-vMyc | + | Blue |
|   | c | LexA-Gal4 | + | Blue |

The results of the above table indicate that none of the tested compounds inhibit the growth of any of the yeast strains. Only compound Z inhibits vFos activity without inhibiting Gal4, and only compound Y inhibits vMyc activity without inhibiting Gal4. Compound X inhibits both vMyc and Gal4 suggesting that it is not specific for the oncoprotein. Compound W does not inhibit oncoprotein induced transcription or Gal4 induced transcription suggesting that compound W is not a transcriptional inhibitor of these proteins.

From these results, compound Z and compound Y would be selected for further investigation such as dose/concentration effects and in vivo studies in animals bearing tumors.

Moreover, a compound need not abolish β-glaactosidase activity to be considered useful in the invention. A compound which reduces the oncoprotein's wild-type level of activity (i.e., level of gene activation) is also selected for further investigation. Such compounds are identified as those which produce a "light blue" result (i.e., lighter than the wild-type "blue" color) upon contact with the yeast host cells.

Example 6

Identification of an Inhibitor of vFos or vMyc in Mammalian Cells

To identify inhibitors which interfere with Fos-mediated or Myc-mediated transcriptional activation in mammalian cells, NIH3T3 cells are transfected with two plasmids. One plasmid is an expression vector that directs the synthesis of a fusion protein from the RSV LTR. LexA-vFos and LexA-vMyc expression plasmids are described above; because activation by LexA-vMyc in mammalian NIH3T3 cells can only be measured using the truncated 202vMycΔC fusion protein (see above), this vector is preferred for use in the assay described in this example. The second plasmid is a "target" that carries a LexA operator upstream of a β-globin promoter fused to the chloramphenicol acetyltransferase (CAT) gene (see above). Gene activation is assayed by measuring CAT activity normalized to the amount of total cellular protein. Gene activation may be assayed using transient or stable transfectants (as described above). Compounds which inhibit activation by LexA-vFos or LexA-vMyc, but which do not inhibit activation by LexA-Gal4, are selected as specific inhibitors of Fos or Myc activity. In one particular example, three NIH3T3 host lines are constructed: host 'a' expressing a LexA-vFos fusion oncoprotein; host 'b' expressing a LexA-vMyc fusion oncoprotein (lacking the Myc dimerization domain); and host 'c' expressing a LexA-Gal4 fusion protein; all cell lines contain a construct possessing the LexA operator upstream of a β-globin promoter fused to the chloramphenicol acetyltransferase (CAT) gene.

TABLE 2

Identification of Oncoprotein Inhibitors

| Compound | NIH3T3 host | Regulatory Protein | Cell Growth | CAT Activity |
|---|---|---|---|---|
| W | a | LexA-vFos | + | yes |
|   | b | LexA-vMycΔC | + | yes |
|   | c | LexA-Gal4 | + | yes |
| X | a | LexA-vFos | + | yes |
|   | b | LexA-vMycΔC | + | no |
|   | c | LexA-Gal4 | + | no |
| y | a | LexA-vFos | + | yes |
|   | b | LexA-vMycΔC | + | no |
|   | c | LexA-Gal4 | + | yes |
| Z | a | LexA-vFos | + | no |
|   | b | LexA-vMycΔC | + | yes |
|   | c | LexA-Gal4 | + | yes |

The results of the above table indicate that none of the tested compounds inhibit the growth of any of the host cells. Only compound Z inhibits vFos activity without inhibiting Gal4, and only compound Y inhibits vMyc activity without inhibiting Gal4. Compound X inhibits both vMyc and Gal4 suggesting that it is not specific for the oncoprotein. Compound W does not inhibit oncoprotein-induced transcription or Gal4-induced transcription suggesting that compound W is not an inhibitor of these proteins.

From these results, compound Z and compound Y would be selected for further investigation such as dose/concentration effects and in vivo studies in animals bearing tumors.

As discussed above, the compound need not abolish CAT activity to be considered useful in the invention. A compound which reduces the oncoprotein's level of CAT activation (i.e., to below wild-type) is also selected for further investigation as an anti-cancer therapeutic.

All references cited herein are fully incorporated by reference. Having now fully described the invention, it will be understood by those with skill in the art that the scope may be performed within a wide and equivalent range of conditions, parameters and the like, without affecting the spirit or scope of the invention or any embodiment thereof.

I claim:

1. A method for testing a compound for the ability to inhibit Myc oncoprotein activity at the level of gene activation potential, said method comprising:

(a) providing a host cell which contains a reporter gene operably-linked to a DNA binding site and which further contains an oncoprotein fusion gene which expresses an oncoprotein fusion protein which comprises a Myc activation domain, lacks a Myc dimerization domain, and which is capable of binding said DNA binding site, wherein the expression of said reporter gene is mediated by said DNA bound oncoprotein fusion;

(b) assaying expression of said reporter gene;

(c) contacting said host cell with said compound; and (d) assaying expression of said reporter gene, a decrease in reporter gene expression in the presence of said compound being indicative of a compound which inhibits Myc oncoprotein activity at the level of gene activation potential.

2. A method for testing a compound for the ability to inhibit Myc oncoprotein activity at the level of gene activation potential, said method comprising:

(a) providing a first host cell which contains a reporter gene operably-linked to a DNA binding site and which further contains an oncoprotein fusion gene which expresses an oncoprotein fusion protein which comprises a Myc activation domain, which lacks a Myc dimerization domain, and which is capable of binding said DNA binding site, wherein the expression of said reporter gene is mediated by said DNA bound oncoprotein fusion;

(b) assaying said reporter gene expression in said first host cell;

(c) providing a second host cell which contains a reporter gene operably-linked to a DNA binding site and which further contains a protein fusion gene which expresses a protein fusion capable of binding said DNA binding site, wherein the expression of said reporter gene is mediated by said DNA bound protein fusion;

(d) assaying said reporter gene expression in said second host cell;

(e) contacting said first host cell and said second host cell with said compound; and (f) assaying expression of said reporter gene in said first host cell and in said second host cell, a greater decrease in reporter gene expression in said first host cell than in said second host cell in the presence of said compound being indicative of a compound which inhibits Myc oncoprotein activity at the level of gene activation potential.

3. The method of either of claim 1 or claim 2, wherein said host cell is selected from the group consisting of yeast and cultured animal cells.

4. The method of claim 3, wherein said host is yeast.

5. The method of claim 4, wherein said yeast is *Saccharomyces cerevisiae*.

6. The method of claim 3, wherein said cultured animal cell is a cultured mammalian cell.

7. The method of claim 6, wherein said cultured animal cell is a monkey kidney CV-1 cell or an NIH3T3 cell.

8. The method of either of claim 1 or claim 2, wherein said reporter gene expression induces a phenotypic change in said host cell.

9. The method of either of claim 1 or claim 2, wherein said reporter gene expression is assayed as chloramphenicol acetyltransferase activity.

10. The method of either of claim 1 or claim 2, wherein said reporter gene expression is assayed as LEU2 activity.

11. The method of either of claim 1 or claim 2, wherein said reporter gene expression is assayed as β-galactosidase activity.

12. The method of claim 8, wherein said phenotypic change is detected by visual inspection of a culture of said host cells.

13. The method of either of claim 1 or claim 2, wherein said DNA binding site is a LexA operator.

14. The method of claim 13, wherein said oncoprotein fusion comprises a LexA DNA binding domain.

15. The method of either of claim 1 or claim 2, wherein said reporter gene expression is further dependent on the activity of a cytoplasmic oncoprotein, a decrease in said reporter gene expression being indicative of a substance which inhibits said Myc oncoprotein or said cytoplasmic oncoprotein.

16. The method of either of claim 1 or claim 2, wherein said reporter gene expression is further dependent on the activity of a membrane-associated oncoprotein, a decrease in said reporter gene expression being indicative of a compound which inhibits said oncoprotein or said membrane-associated oncoprotein.

17. A fusion protein comprising (a) a portion of a Myc oncoprotein, said portion being capable of activating gene expression and lacking a functional Myc dimerization domain, fused to (b) a heterologous DNA binding domain.

18. The fusion protein of claim 17, wherein said Myc portion lacks a Myc helix-loop-helix domain.

19. The fusion protein of claim 17, wherein said heterologous DNA binding domain is a LexA DNA binding domain.

20. DNA encoding a fusion protein of claim 17.

21. A vector comprising the DNA of claim 20.

* * * * *

UNITED STATES PATENT AND TRADEMARK OFFICE
CERTIFICATE OF CORRECTION

PATENT NO. : 5,580,721
DATED : December 3, 1996
INVENTORS : Roger Brent et al.

It is certified that error appears in the above-identified patent and that said Letters Patent is hereby corrected as shown below:

Column 1, line 22, replace "vital" with --viral--;

Column 1, line 39, replace "5:277-292" with --15:277-292--;

Column 2, line 17, after "These" delete the period;

Column 14, line 43, replace "LexA-cMyo" with --LexA-cMyc--;

Column 14, line 52, replace "Sinai site" with --Smal site--.

Signed and Sealed this

Sixteenth Day of September, 1997

Attest:

BRUCE LEHMAN

Attesting Officer

Commissioner of Patents and Trademarks